(12) United States Patent
Mahoney et al.

(10) Patent No.: US 7,347,080 B2
(45) Date of Patent: Mar. 25, 2008

(54) THERMAL CONDUCTIVITY DETECTOR

(75) Inventors: Steve Mahoney, Hillsboro, OR (US); John Hinshaw, Hillsboro, OR (US)

(73) Assignee: Serveron Corporation, Hillsboro, OR (US)

( * ) Notice: Subject to any disclaimer, the term of this patent is extended or adjusted under 35 U.S.C. 154(b) by 122 days.

(21) Appl. No.: 11/318,153

(22) Filed: Dec. 23, 2005

(65) Prior Publication Data

US 2007/0144238 A1 Jun. 28, 2007

(51) Int. Cl.
*G01N 30/66* (2006.01)
(52) U.S. Cl. .................... 73/23.4; 73/23.35
(58) Field of Classification Search ........... 73/23.35, 73/23.4
See application file for complete search history.

(56) References Cited

U.S. PATENT DOCUMENTS

| | | | |
|---|---|---|---|
| 4,038,055 A | * | 7/1977 | Varano et al. ............... 96/102 |
| 4,741,198 A | * | 5/1988 | Farren et al. ............... 73/23.4 |
| 4,813,267 A | * | 3/1989 | Norem et al. ............... 73/23.4 |
| 6,550,961 B1 | | 4/2003 | Ueda |
| 6,890,095 B2 | | 5/2005 | Gul |

FOREIGN PATENT DOCUMENTS

JP 55-94159 A * 7/1980 ................... 422/89

* cited by examiner

*Primary Examiner*—Daniel S. Larkin
(74) *Attorney, Agent, or Firm*—Hancock Hughey LLP

(57) ABSTRACT

A thermal conductivity detector (TCD) utilizes a modular thermistor assembly that mounts to the TCD body. The thermistor assembly is easily replaceable in the TCD. Within the TCD, a thermistor bead is always held in the same relative location in a gas flow path, which is designed to produce laminar, low velocity gas flow across the thermistor bead. Two TCDs, each having a heater, are mounted in an insulated enclosure. The heaters are activated to bring the TCDs to operating temperature, and are then deactivated during analysis.

20 Claims, 5 Drawing Sheets

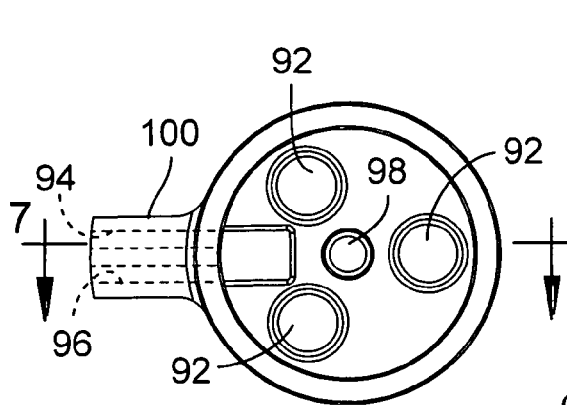
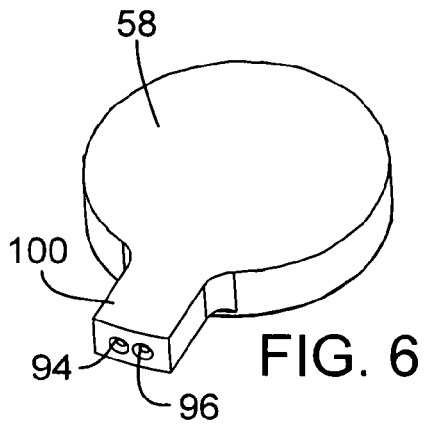
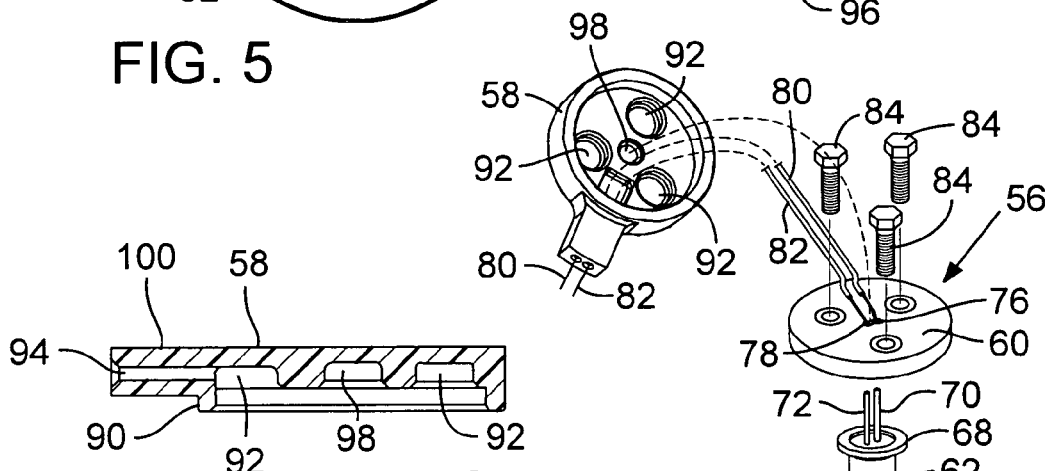
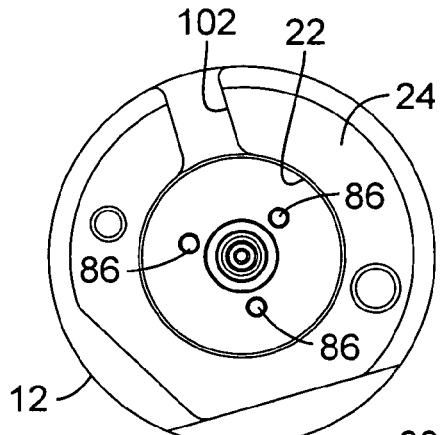
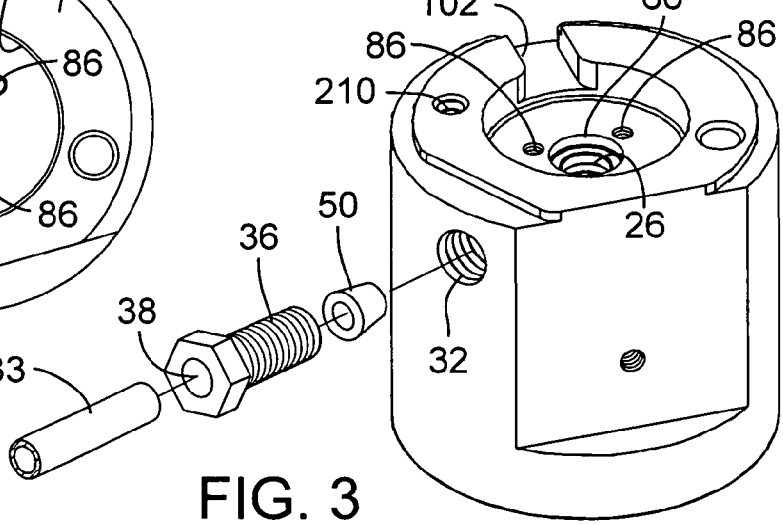

THERMAL CONDUCTIVITY DETECTOR

FIELD OF THE INVENTION

The present invention relates to thermal conductivity detectors for use in gas chromatographs, and more specifically to a thermal conductivity detector using a thermistor bead assembly.

BACKROUND

Thermal conductivity detectors (TCDs) have been used as detectors in gas chromatographs for many years. A TCD essentially consists of an electrically heated filament wire or thermistor that is held in a stream of flowing gas. The heated wire acts as a temperature-sensing element. The temperature of the sensing element varies depending upon the thermal conductivity of the gas flowing around it. Changes in thermal conductivity, for example, when organic molecules are entrained in the carrier gas, cause a change in the temperature of the sensor element, which is typically detected as a change in electrical resistance in the element. Typically, the change in resistance is detected and measured in a bridge circuit as a voltage change.

In a typical gas chromatograph, two pairs of TCDs are used. The first pair is placed in a gas stream of the column effluent to detect the separated chemical components as they leave the column. The other pair is located upstream of the injector or at the outlet of a separate reference column. The two sets of pairs are arranged in a bridge circuit, which allows amplification of resistance changes that result from differences in the thermal conductivity between the two gases flowing through the pair of TCDs. In another arrangement, fixed resistors are substituted for the two of the TCD cells in the bridge circuit. Voltage changes in the circuit may be used to quantify and qualify various chemical components in the sample.

In any analytical instrument such as a GC, it is very important that the components used in the instrument are as robust as possible. For example, gas fittings in the GC must be leak free and able to withstand prolonged exposure to harsh environments. This is especially true in analytical instruments that are intended for operation in field conditions, often remotely. Unlike the controlled environment of a laboratory, analytical instruments used in the field are subjected to wide temperature variations and other environmental extremes.

Thermistor beads have been advantageously used as the temperature sensing elements in a TCD, and there are several methods of mounting the thermistor beads in the gas path, including using metallic gaskets and compression fittings. However, these methods are complicated and require numerous and expensive parts. Moreover, these methods are prone to development of leaks, and do not accurately position the thermistor consistently in the gas flow, which may lead to variations in readings obtained from the instrument.

The present invention relates to a TCD that utilizes a thermistor bead assembly for the temperature-sensing element. The thermistor bead is mounted in a modular thermistor assembly that is easily assembled in the TCD manifold, and consistently and repeatedly positioned in the desired location in the gas stream.

BRIEF DESCRIPTION OF THE DRAWINGS

The invention will be better understood and its numerous objects and advantages will be apparent by reference to the following detailed description of the invention when taken in conjunction with the following drawings.

FIG. 3 is another perspective view of the TCD according to the present invention, illustrating some of the primary components in the TCD in an exploded view.

FIG. 4 is a top plan view of the of the thermistor body used in the present invention, showing the configuration of the axial bore through the body.

FIG. 5 is a bottom plan view of the protective silicon boot.

FIG. 6 is a top perspective view of the silicon boot shown in FIG. 5.

FIG. 7 is a cross sectional view of the protective silicon boot, taken along the line 7-7 of FIG. 6.

DETAILED DESCRIPTION OF THE PREFERRED EMBODIMENTS

Figure 1:
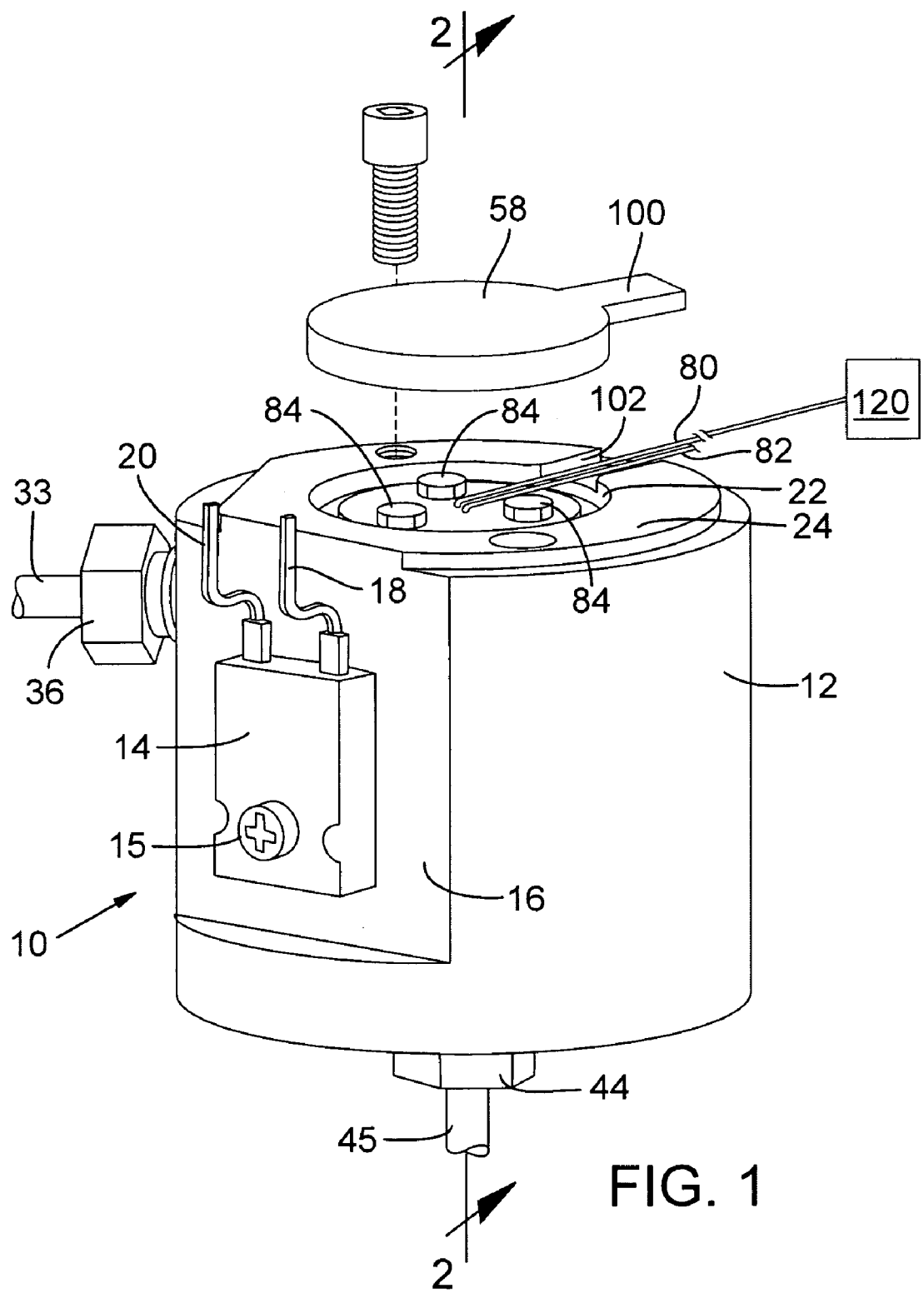
FIG. 1 is a perspective, partially exploded view of a thermal conductivity detector according to the present invention.

A preferred embodiment of a TCD 10 is shown in the drawings. TCD 10 comprises a generally cylindrically shaped monolithic body 12 that is preferably a machined solid piece of metal with a large thermal mass such as stainless steel, that has a relatively high density and also has a high heat capacity. A resistive heater 14 is mounted with a screw 15 to a planar surface 16 that is machined into body 12. Heater 14 is connected to a power source (not shown) through conductors 18, 20. A circular recess 22 is formed in the upper surface 24 of body 12 for receiving the thermistor head, as detailed below.

Figure 2:
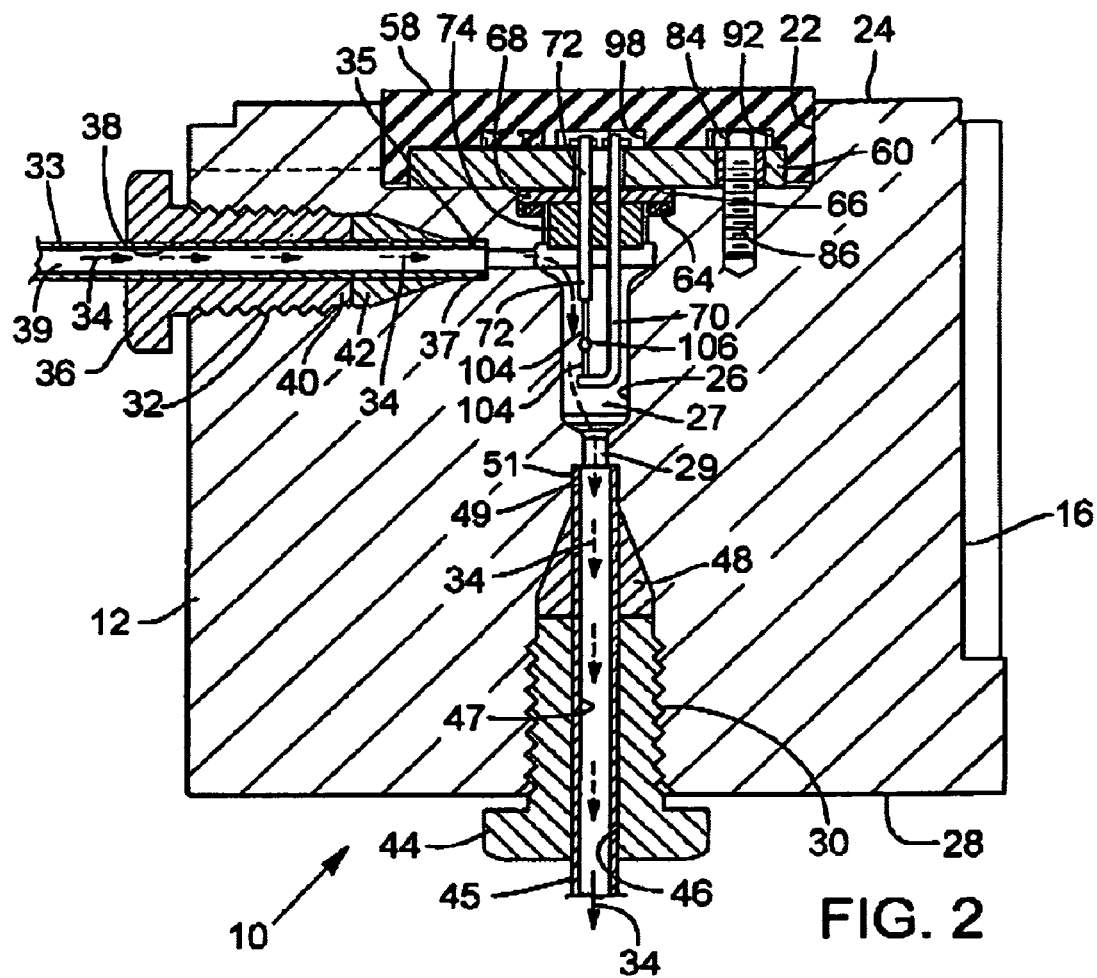
FIG. 2 is a cross sectional view of the TCD shown in FIG. 1, taken along the line 2-2 and showing the section with some of the primary TCD components installed.

With reference now to FIG. 2, an axial bore 26 is formed entirely through body 12, through the center of circular recess 22 and exiting though the base 28 of the body at a threaded opening 30. As detailed below, the axial bore 26 is specifically shaped along its length to accommodate components of TCD 10, and to facilitate laminar flow of gas through the bore, including a chamber 27. An inlet bore 32 is formed in body 12 in a direction transverse to axial bore 26, and intersects axial bore 26 to define a gas flow path 34 (represented with arrows in FIG. 2) from inlet tubing 33 through chamber 27 and the outlet, described below. Inlet bore 32 is threaded to receive a threaded nut 36 that has a longitudinal bore 38 through the center of the nut and a ferrule 42 on the inner end. Inlet tubing 33 has a central gas-carrying passageway 39 and the tubing extends through bore 38 in nut 36, and the inner end 35 of tubing 33 abuts an annular rim 37 formed in inlet bore 32. The opposite end of tubing 33 is attached to the outlet of a chromatographic column (not shown). When nut 36 is tightened in bore 26 the nut compresses ferrule 42, thereby making a gas-tight connection between the inner end 35 of inlet tubing 33 with the annular rim 37 so that gas flowing from a chromatographic column is directed into passageway 38 and thus into gas flow path 34.

Similarly, the outlet from body 12 is defined by a threaded nut 44 that has a longitudinal bore 46 extending therethrough. Outlet tubing 45 has a central gas-carrying passageway 47 and the tubing extends through bore 46 in nut 44. The inner end 49 of tubing 45 abuts an annular rim 51 formed in bore 46. The opposite end of tubing 45 is either vented to atmosphere or through an appropriate vent such as a frit restrictor. When nut 44 is tightened in bore 46 the nut compresses a ferrule 48, thereby making a gas-tight connection between the inner end 49 of outlet tubing 45 with the annular rim 51 so that gas flowing through gas flow path 34 exits TCD 10.

Gas flow path 34 begins at the bore 39 in inlet tubing 33, flows into chamber 27 and into a constriction 29 in axial bore 26. Constriction 29 represents a section of the axial bore having a smaller diameter than chamber 27—the diameter of the axial bore tapers smoothly from a relatively larger diameter in chamber 27 to the relatively smaller diameter in constriction 29. The flow path then continues through bore 47 of outlet tubing 45.

Turning now to FIG. 3, thermistor assembly 56 will be detailed. Thermistor assembly 56 comprises a boot 58, a cap member 60, a bead thermistor 62 and an O-ring gasket 64, all of which are adapted for insertion into axial bore 26 and circular recess 22 as indicated in FIG. 3. Specifically, O-ring gasket 64 is received on an annular shelf 66 formed in axial bore 26. Bead thermistor 62 has an upper annular ring 68 that is sized to fit into annular shelf 66. Thermistor 62 further includes two conductors 70, 72 that extend through the main body 74 of the thermistor and, when cap member 60 is assembled with thermistor assembly 56, through openings 76 and 78, respectively, in the cap member. Conductors 70 and 72 are supported by cap member 60 and are electrically connected to lead wires 80 and 82, respectively, which lead through boot 58 and are connected to the control electronics in controller 120 (shown schematically in FIG. 1).

Cap member 60 defines a circular disk that is slightly smaller in diameter than circular recess 22. The cap member is preferably fabricated from a durable, insulator plastic such as many PCB substrate materials, and is retained in circular recess 22 with three screws 84. When screws 84 are tightened into threaded openings 86, the screws tighten cap member 60 against body 12, thereby urging the annular ring 68 of bead thermistor 62 into O-ring gasket 64, compressing the gasket (see FIG. 2) and creating a leak-free seal.

As shown in FIGS. 5 through 7, boot 58 is a protective member that covers cap member 60 and protects wires 80 and 82. Boot 58 is preferably made from a deformable silicon material that provides both a thermal insulator for the thermistor and acts as a strain relief for wires 80 and 82. The sectional view of FIG. 7 shows that boot 58 includes a downwardly depending rim portion 90 that is sized to fit around the perimeter of cap member 60 when the cap member is mounted to body 12 in circular recess 22. The outer circumference of boot 58 is nearly the same as circular recess 22 so the boot fits snuggly into the recess. Cavities 92 are positioned in boot 58 to receive the heads of screws 84. A central cavity 98 is positioned to receive conductors 70 and 72 where they exit cap member 60 and are electrically connected to lead wires 80 and 82. A pair of lead wire openings 94 and 96 is provided for lead wires 80 and 82; the lead wire openings extend through an extended portion 100 of boot 58. Extended portion 100 fits into a notch 102 in body 12. It will be appreciated that the combination of extended portion 100 and notch 102 functions as a positive locating system for the thermistor assembly 56. Each time a thermistor assembly is removed and replaced in body 12, the assembly is located in the body in same position and orientation relative to the body and the thermistor 106 is therefore always positioned in chamber 27 is a desired location.

Conductors 70 and 72 of bead thermistor 62 are attached to respective opposite ends of thin conductive filament 104, which has a thermistor bead 106 attached to the filament approximately midway along its length. The conductors thus serve to electrically connect and support the thermistor bead in chamber 27. Thermistor bead 106 functions as the temperature-sensing element in TCD 10 and when the thermistor assembly 56 is mounted in body 12 as shown in FIG. 2, thermistor bead 106 is suspended in a chamber 27 in gas flow path 34.

In operation, a chromatographic column is coiled around the exterior surface of body 12 in contact with the surface. Since heater 14 is mounted on planar surface 16 the chromatographic column may be smoothly coiled around the body without interference from the heater. The inlet to the chromatographic column is attached to instruments that facilitate injection of gas (either sample gas or carrier gas) into the column, and the outlet end of the column is connected to the internal threads at the proximal end of longitudinal bore 32. At the opposite end of the gas flow path 34, outlet tubing is connected to the internal threads at the proximal end of longitudinal bore 46. An optional vacuum pump may be placed in-line at the outlet tubing.

In order to minimize temperature fluctuations in the TCD, which could result in background noise during analysis, the combination of the body 12 and the chromatographic column are wrapped with insulating material as detailed below with respect to FIGS. 8 and 9. The insulated TCD 10 is suspended in a constant temperature oven in the GC. By suspending the TCD within the GC oven without direct contact between the TCD and the oven walls, as detailed below, the TCD is thermally and mechanically isolated from the relatively cooler temperatures that typically are found at the edges of the oven. There is also less chance of direct heat transfer from the oven walls to the TCD. The insulation jacket 122 around heated body 12 limits the flux of heat that is conducted into or out of the surrounding heated GC oven. As a result, when cold-starting the unit the time required for the heated body 12 to reach operating temperature may be longer than desired.

When resistive heater 14 is energized, heat is radiated through body 12, which as noted is fabricated from a metal that is selected for its good thermal conductivity properties. As the detector body heats to operating temperature due to heat from the resistive heater 14, the internal detector body temperature is monitored by the microprocessor controller 120 using the resistance of thermistor bead 106 at low power as a temperature measuring device. Once the heated body 12 has reached the GC oven temperature the resistive heater 14 may be de-energized and the heated detector body temperature is then maintained entirely by heat conduction from the GC oven through the coaxial insulating jacket 122. This arrangement provides for a more constant internal detector body temperature compared to active heating and control of the heated body with resistive heater 14, and in turn reduces the detector electrical signal noise due to thermal fluctuations compared to other detector designs in which the detector is located proximally to the GC oven and heated by separately controlled heater/temperature sensor circuits.

The insulated, heated body 12, in combination with the body being suspended in an oven in the GC that is heated to the same temperature, minimizes fluctuation of the temperature of gas flowing through gas flow path 34. This minimizes variance in analytical results due to temperature fluctuation. When TCD 10 is being used to test a fluid sample, electrical current is continuously flowing across thermistor bead 106, which heats the bead.

A stream of gas is introduced into gas flow path 34 from the GC column, which as noted is connected to nut 36. With reference to FIG. 2, it may be seen that gas flow path 34 turns approximately 90° where inlet bore 32 meets axial bore 26. As the gas stream flows around this corner (as shown with the arrows in FIG. 2 representing the gas flow path 34), the velocity of the gas decreases significantly. The velocity of gas is further decreases by constriction 29 in axial bore 26, which as shown in FIG. 2 is just downstream of chamber 27 and hence thermistor bead 106. The pressure of the gas entering body 12 at inlet bore 32 is only very slightly above the pressure of the gas out the outlet, at nut 44, which typically at atmospheric pressure, or less, if a vacuum pump is connected. Gas flow through flow path 34 is highly laminar. This is a result of the relatively low pressure drop through flow path 34 and the relatively low velocity flow. The tapering of axial bore 26 from chamber 27 through constriction 29 also contributes to a highly laminar flow where the gas passes over thermistor bead 106. Non-laminar gas streams are known to cause analytical noise. Accordingly, the combination of very constant temperature and highly laminar, low velocity gas flow in TCD 10 results in minimal noise.

As described earlier, as a stream of flowing gas passes over the thermistor, the thermistor acts as a temperature sensing element. Controller 120 is a microprocessor programmed for controlling operations of the GC and TCD 10. The temperature of the sensing element—bead 106—varies depending upon the thermal conductivity of the gas flowing around it. When the chemical composition of the carrier gas changes, a change in the temperature of the sensor element results. This is detected as a change in resistance in the thermistor bead. The change in resistance is converted to a voltage change, which is then detected and measured in a bridge circuit.

With the TCD 10 described above, the thermistor bead 106 is always mounted in the same relative position in chamber 27. When the thermistor assembly 56 needs to be replaced, the entire unit is replaced in the same orientation, and as a result of the extended portion 100 of boot 58 engaging notch 102, the bead 106 of the replacement thermistor assembly will be in the same location in chamber 27 as the bead in the prior unit. The thermistor assembly 56 is easily removed and replaced.

Figure 8:
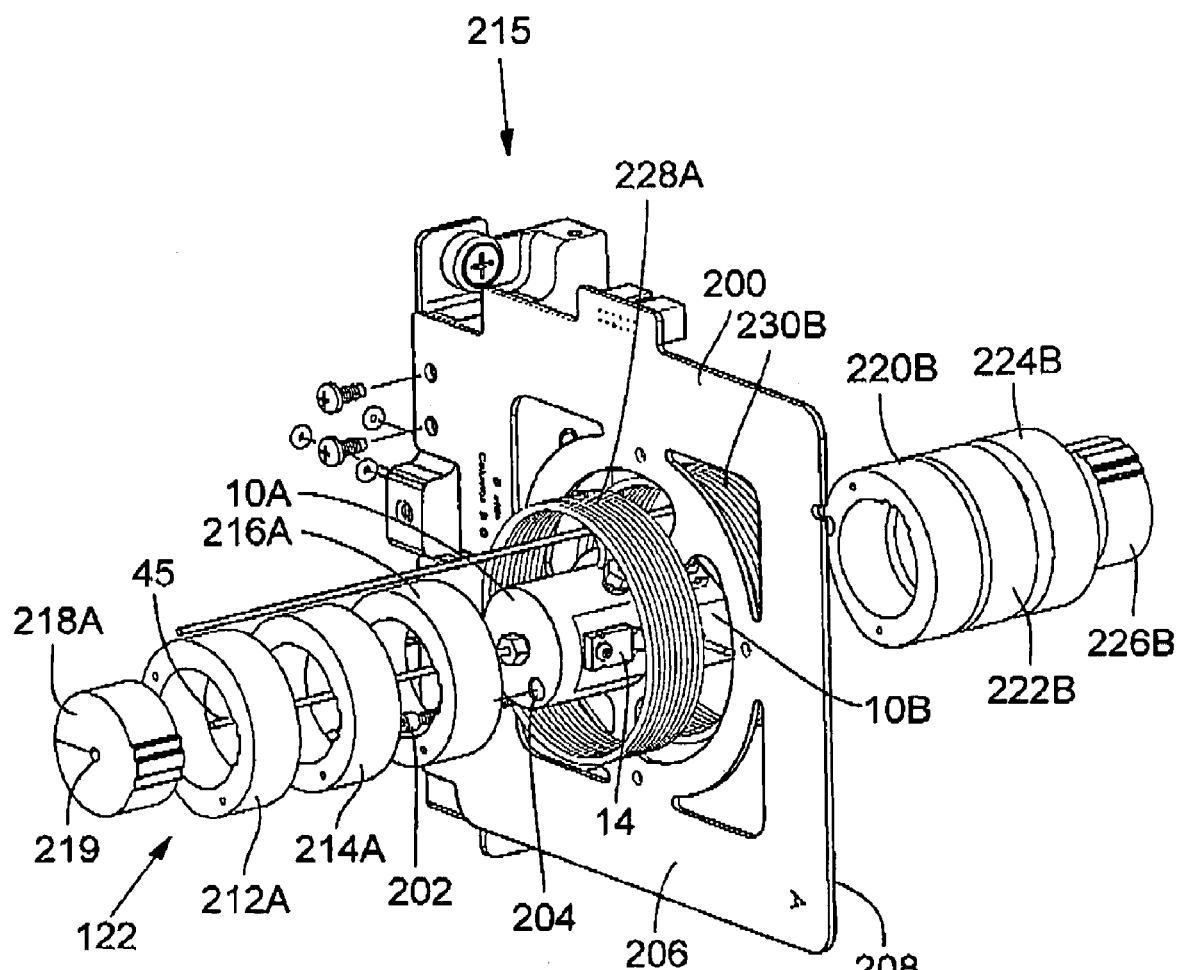
FIG. 8 is a perspective, exploded view of the TCD according to the present invention shown as it is mounted.
Figure 9:
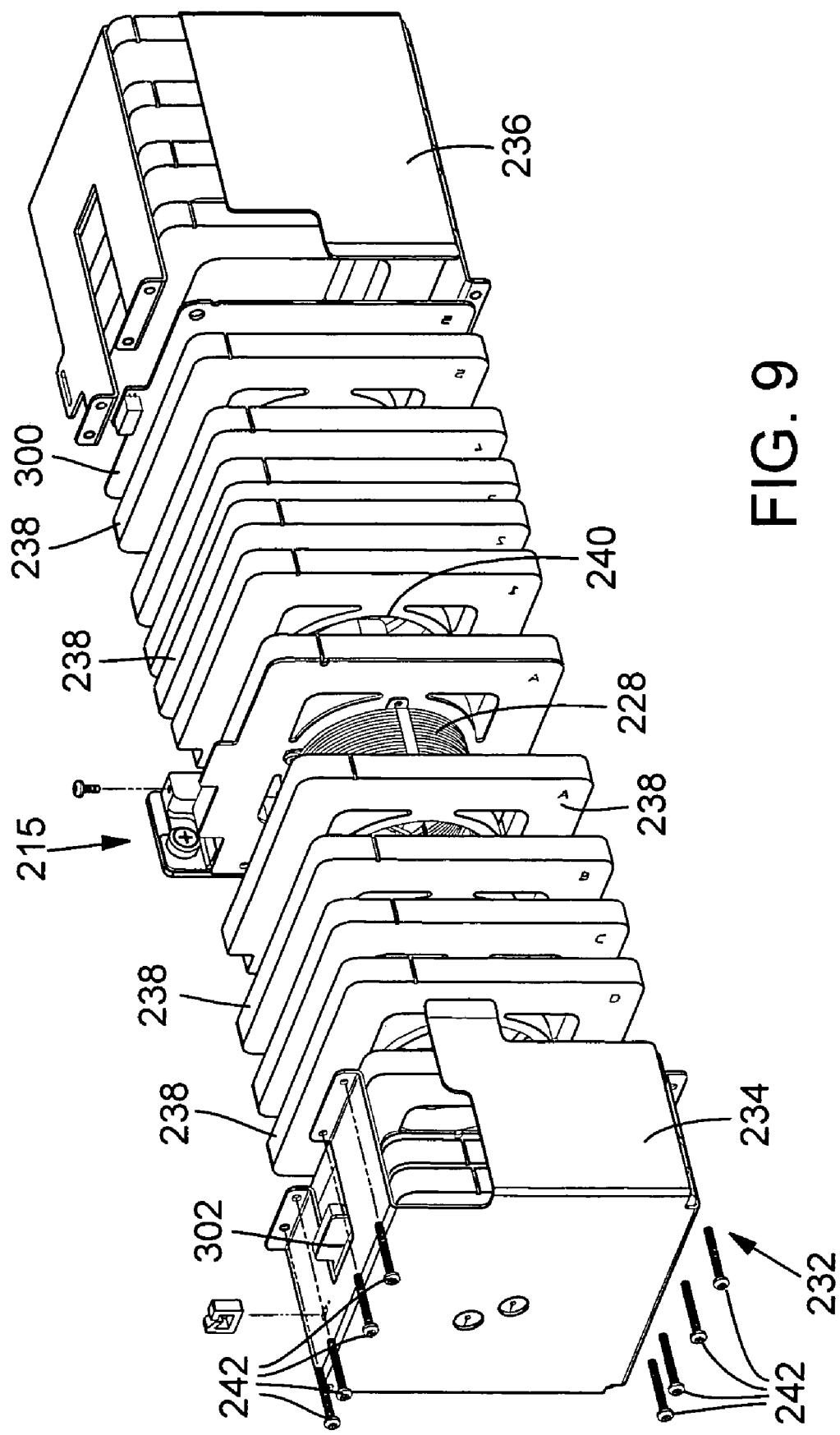
FIG. 9 is a perspective, exploded view of the TCD and mounting systems shown in FIG. 8, and including GC housing and insulation elements.

With reference now to FIGS. 8 and 9, the preferred structure and method for assembling the TCD 10 described in a GC will be described. As shown in FIG. 8, a first TCD 10A is mounted to a first side 206 a printed circuit board 200 with a screw 202 that extends through a bore 204 that is formed through body 12. PCB 200 is preferably fabricated from a highly thermally insulative material such as fiberglass. A second TCD 10B is mounted to the opposite side of PCB 200. Screw 202 extends through bore 204 in the first TCD 10A, and threads into a threaded bore 210 in second TCD 10B (see FIG. 3). Similarly, but not shown in the perspective view of FIG. 8, a second screw extends through a bore in second TCD 10B and into a cooperatively positioned threaded bore in TCD 10A. The PCB 200 lies between and separates TCD 10A and 10B when they are mounted as indicated. The assembly shown in FIG. 8 is referred to as the TCD assembly 215.

Cylindrical insulation sleeves 212A, 214A and 216A have internal diameters designed to closely conform to the outer surface of TCD 10A and a slid over and thus wrap the TCD when mounted to PCB 200. A cap insulator 218A includes a bore 219 for receiving tubing 45 and is mounted to the end of TCD 10A. Likewise, insulation sleeves 220B, 222B and 224B are slid over TCD 10B and a cap insulator 226 is installed.

As seen in FIG. 8, the insulating sleeves slide over the heater 14. Chromatographic column 228A is coiled around the outer surface of the combined insulation sleeves 212A, 214A and 216A, and a chromatographic column 230B is similarly coiled around the outer surface of the insulation sleeves on TCD 10B.

The various structural and electrical connections between the TCD 10A and 10B are made (for example, to sample sources, calibration gas sources, carrier gasses, etc.) and the TCD assembly 215 is assembled in GC oven 232, as shown in FIG. 9. GC oven 232 includes opposed end assemblies 234 and 236. Plural insulation boards 238 are held sandwiched in GC oven 232. Each insulation board 238 has a cylindrical central opening 240 that has a diameter that is sized to approximate the diameter of the coiled chromatographic columns 228 and 230. As such, when the insulation boards are stacked onto the TCD assembly 215 as shown, the columns 228 and 230 lie in close tolerance to central openings 240. Opposed end assemblies 234 and 236 are attached to one another with screws 242.

GC oven 232 provides a highly insulative housing for the TCDs 10A and 10B. The TCDs 10A and 10B are not in physical contact with the sides of the GC oven end assemblies. As such, the TCDs are essentially suspended in the oven 232 without making contact with any non-insulating material.

In operation, when the system is cold-started, heaters 14 are activated by microprocessor 120 to begin bringing the TCDs 10 up to operating temperature. During this period, a relatively low voltage is applied across thermistor bead 106 and the thermistor is thus utilized as a temperature sensor for determining the temperature of the apparatus. The heaters 14 bring the TCDs up to operating temperature rapidly. Once a predetermined operating temperature is reached, as determined with thermistor bead 106, power to heaters 14 is turned off and the temperature is maintained by the primary heater and air circulation circuit. No analysis is performed during the time when heaters 14 are energized; this mode is referred to herein as the cold start heating mode.

When the predetermined operating temperature is reached and stabilized the, sample analysis may be begun. This is referred to as the analysis mode. In the analysis mode, thermistor bead 106 is used in the manner described previously to detect analytes in a sample. Those of skill in the art will understand that two TCDs 10A and 10B are used for comparative analytical processing.

Because TCDs 10A and 10B reside in a highly insulative enclosure defined by GC oven 232, analytical results are highly precise. In the analysis mode, heaters 14 are never activated. As such, the TCDs are always passively heated during the analysis mode. As noted, there is no active heating of the TCDs during the analysis mode—heaters 14 are actively heating the TCDs only during the cold start heating mode. This, combined with the high insulating values provided by oven 232 results in very little "noise" that would otherwise be caused by temperature variations.

The temperature stability of the TCD depends on the stability of the internal temperature of Oven 232, which is preferably established and maintained by a heater/fan assembly 300 and independent thermal sensor 302 under the control of microprocessor 120. Various control schemes are suitable, including for example a proportional-integral-differential (PID) type of control system.

While the body 12 is illustrated in a preferred embodiment as being substantially cylindrical, it will be appreciated that the body could have any three dimensional configuration such as a cube, or other shape.

While the present invention has been described in terms of a preferred embodiment, it will be appreciated by one of ordinary skill that the spirit and scope of the invention is not limited to those embodiments, but extend to the various modifications and equivalents as defined in the appended claims.

We claim:

1. A thermal conductivity detector for use with a chromatograph, comprising:
    a body having an axial bore therethrough, said bore defining a chamber having a first diameter and an outlet having a second diameter that is less than the first diameter, wherein the chamber diameter tapers smoothly from the first diameter to the second diameter; and said chamber further including an inlet defined by a bore extending through said body substantially transverse to the axial bore;
    said inlet bore, chamber and outlet bore defining a gas flow path through said body;
    a cap affixed to one end of said body and supporting first and second conductors extending through said cap and into said chamber;
    a thermistor bead electrically connected between said first and second conductors in said chamber; and
    a heater attached to an outer surface of said body.

2. The thermal conductivity detector according to claim 1 wherein said cap is received in a seat formed in said body and forms a gas-tight seal with said body.

3. The thermal conductivity detector according to claim 2 wherein said cap is assembled with a protective boot that defines thermistor bead locator means for positioning said thermistor bead in a predetermined position in said chamber.

4. The thermal conductivity detector according to claim 3 wherein said thermistor bead locator means further comprises a notch in said body and an extended portion of said boot, wherein said extended portion is received into said notch.

5. The thermal conductivity detector according to claim 4 wherein said boot may be assembled with said cap in only one relative orientation between the cap and the boot.

6. The thermal conductivity detector according to claim 1 including a gas source connected to said inlet with a gas-tight fitting and wherein gas entering said flow path exhibits laminar flow through said chamber past said thermistor bead.

7. The thermal conductivity detector according to claim 1 including a controller configured for detecting voltage changes across said thermistor bead for determining in a first operational mode the temperature of said body and in a second operational mode quantifying chemical constituents in a sample of gas flowing in the gas flow path.

8. A thermal conductivity detector assembly for use with a chromatograph, comprising:
    a first detector having a body having a flow path therethrough, said flow path including an inlet, a chamber and an outlet, said chamber and outlet extending longitudinally along the axis of said body and said inlet defined by a bore extending through said body substantially transverse said axis; a chromatographic column fluidly connected to said inlet; a cap affixed to one end of said body and supporting first and second electrical conductors extending into said chamber and electrically connecting a thermistor bead in said chamber; a heater attached to an outer surface of said body; insulation surrounding said body on all sides except one end; and said body having one end mounted to a thermally insulated mounting board; and
    a second thermal conductivity detector having body having a flow path therethrough, said flow path including an inlet, a chamber and an outlet, said chamber and outlet extending longitudinally along the axis of said body and said inlet defined by a bore extending through said body substantially transverse said axis; a chromatographic column fluidly connected to said inlet; a cap affixed to one end of said body and supporting first and second electrical conductors extending into said chamber and electrically connecting a thermistor bead in said chamber; a heater attached to an outer surface of said body; insulation surrounding said body on all sides except one end, and said body mounted to an opposite side of said thermally insulated mounting board.

9. The thermal conductivity detector assembly according to claim 8 wherein both first and second detectors are wrapped in insulation and housed in an enclosure, and wherein the only source of heat in the enclosure is said heaters attached to said bodies.

10. The thermal conductivity detector assembly according to claim 9 operable in a first mode in which said heaters are activated and said thermistor beads are used to detect the temperature of the detector bodies, and a second mode in which said heaters are deactivated and said thermistor beads are used to analyze a sample.

11. The thermal conductivity detector assembly according to claim 10 wherein the heaters are never activated in the second mode.

12. The thermal conductivity detector according to claim 8 wherein each detector further comprises thermistor bead locating means for positioning said thermistor in a predetermined location in said chamber.

13. The thermal conductivity detector according to claim 12 wherein each thermistor bead locating means comprises a cap affixed to one end of said body and supporting first and second conductors extending through said cap and into said chamber, and a boot assembled with said cap, wherein a portion of said boot is received in a notch in said body so that said cap may be affixed to said body in only one orientation.

14. In a chromatograph using a thermal conductivity detector with a thermistor bead, the method of operation comprising the steps of:
    a) operating the chromatograph in a first operational mode during which the detector is heated and no analysis is being performed, sensing the temperature of the detector during the first operational mode with the thermistor bead; and
    b) operating the chromatograph in a second operational mode during which the detector is not heated and analysis is performed with the thermistor bead.

15. The method of claim 14 including the steps of:
    providing first and second thermal conductivity detectors, each having a substantially cylindrical body with first and second opposite ends and each having a heater mounted to an outer surface of the body, each detector further including a thermistor bead in a gas flow path electrically connected to a controller;
    mounting said first and second detectors on opposite sides of a thermally insulative board by connecting the first end of the first detector to the first end of the second detector with the thermally insulative board disposed therebetween;

insulating each detector with a first insulation layer;

connecting a chromatographic column to an inlet into each detector and coiling each column around the insulated detector to which the column is attached; and insulating the column and the detector with a second insulation layer.

16. The method of claim 15 in which during the first operational mode no analysis is performed.

17. The method of claim 16 in which during the second operational mode the heaters are inactivated.

18. The method according to claim 15 including the step of locating the thermistor bead in a predetermined location in the gas flow path.

19. The method according to claim 18 wherein the step of locating the thermistor bead includes the step of installing a thermistor cap assembly on the body in a predetermined desired orientation.

20. The method according to claim 15 including the step of suspending the detectors in an enclosure.

* * * * *